Nov. 23, 1965 E. G. FISHER Plant Pat. 2,576
ROSE PLANT
Filed Sept. 29, 1964
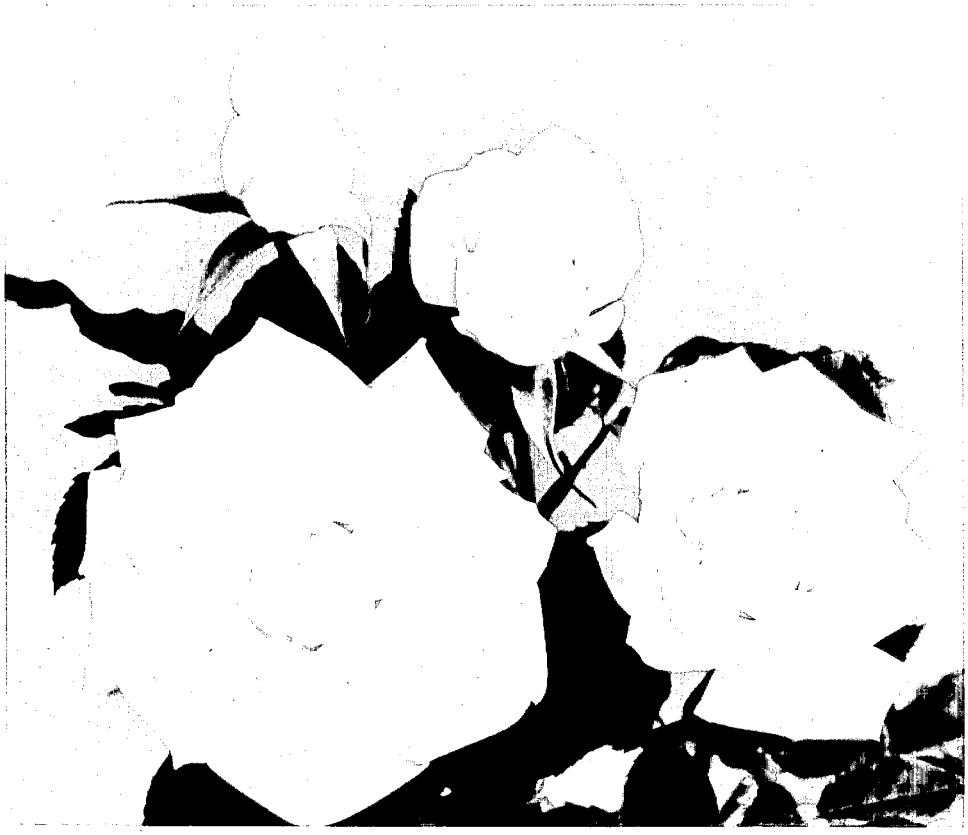
INVENTOR
ESTHER GLADYS FISHER
Brown, Jones, Benedict, Sandell & Miller
ATTORNEYS United States Patent Office Plant Pat. 2,576
Patented Nov. 23, 1965

2,576
ROSE PLANT

Esther Gladys Fisher, Woburn, Mass., assignor to The Conard-Pyle Company, West Grove, Pa., a corporation of Pennsylvania Filed Sept. 29, 1964, Ser. No. 400,277
1 Claim. (Cl. Plt.—24)

This invention relates to a new and distinct variety of rose plant of the floribunda class which was originated by me by crossing Golden Anniversary (Plant Patent No. 806) with Masquerade (Plant Patent No. 975).

The primary objective of this breeding was to create a distinct variety of rose different from all other known varieties of roses in several important characteristics.

This new variety is distinct from all varieties of roses of which I am aware in the following combination of characteristics:

(1) A plant of good vigor and balanced habit.

(2) Flowers which at certain times of the year can be extraordinarily large for a plant of the floribunda class.

(3) An unusually good continuity of bloom.

(4) A petal count of from 40 to 45.

(5) The color of the flowers which varies from Mimosa Yellow in newly opened blooms to Barium Yellow at maturity.

Asexual reproduction of my new variety by budding was performed in West Grove, Pennsylvania, and shows that the above-mentioned characteristics and distinctions come true to form and are established and transmitted through succeeding propagation.

The accompanying drawing shows typical specimens of the flowers and foliage of my new variety in different steps of development and as depicted in color as nearly true as is reasonably possible to make the same in a color illustration of this character.

The following is a detailed description of my new variety with color terminology in accordance with the color chart of the Royal Horticultural Society:

Type: Hardy; bush, outdoor; seedling; for garden decoration.
Class: Floribunda.
Propagation: It does hold its distinguishing characteristics through succeeding propagations by budding.

*The flower*

Locality where grown: West Grove, Pennsylvania.
Flowers borne: Several to stem; in irregular cluster; on normal medium stems.
Quantity of bloom: Abundant, outdoors.
Continuity: Continuous.
Fragrance: Slight; sweetbriar.
Bud:

*Peduncle.*—Medium length, medium size; erect; medium green; rough; numerous; glandular hairs; red.

*Before calyx breaks.*—Size—medium. Form—pointed ovoid with a conspicuous neck; with foliaceous appendages on the surface of the bud; with bristle-like foliaceous parts extending beyond the tip of the bud equal to ¾ or more of its length.

*As calyx breaks.*—Color—Pod Green 061 overlaid with Claret Rose 021/1.

*As first petal opens.*—Size—medium. Form—medium-pointed, ovoid. Color: outside—Aureolin 3 over lower half of petal grading to Aureolin 3/3 at apical margin, usually irregularly marked with Erythrite Red 0027/2; inside—Lemon Yellow 4 at base becoming progressively paler towards upper margin where dominant color is Naples Yellow 403/3.

*Opening.*—It does open up well.

Bloom:

*Size when fully open.*—Large, 4½ inches to 4¾ inches.

*Petalage.*—Double; from 40 to 45 petals; arranged regularly.

*Form.*—High-centered at first; becoming cupped; petals remaining at first loosely rolled outward; becoming later at maturity loosely rolled outward.

Petals: Medium soft; with inside satiny; outside shiny.

*Shape.*—Outer—obovate; no notches. Intermediate—obovate; no notches. Inner—undulate; irregular; no notches.

This description of a newly opened flower was made from a rose grown outdoors in October 1963, at West Grove, Pennsylvania.

*Color.*—Outer petal: outside surface—Barium Yellow 503 at base of petal becoming progressively paler with upper half of petal Primrose Yellow 601/3; inside surface—base of petal Aureolin 3 becoming progressively lighter towards the outer margin of the petal the color of which is Mimosa Yellow 602/1. Intermediate petal: outside surface—base of petal Barium Yellow 503 changing to Barium Yellow 503/1 which is the dominant color over the remainder of the petal; inside surface—base of petal Aureolin 3 becoming progressively lighter towards the outer margin the color of which is Mimosa Yellow 602/1. Inner petal: outside surface—base of petal Barium Yellow 503 gradually changing to Barium Yellow 503/1 over the upper half of the petal; inside surface—base of petal Aureolin 3 gradually changing to Mimosa Yellow 602/1 at the outer margin.

This description was made from a rose that was open for three days outdoors, in October 1963, at West Grove, Pennsylvania.

*Color.*—Outer petal: outside surface—Barium Yellow 503 covering lower half of petal then changing to Canary Yellow 2/3 over upper half of petal; inside surface—Aureolin 3/1 at base of petal changing to Aureolin 3/2 and to Canary Yellow 2/3 covering the upper quarter of the petal. Inner petal: outside surface—Barium Yellow 503 at base becoming Barium Yellow 503/1 over remaining ⅘ of petal; inside surface—Aureolin 3 at base of petal becoming progressively lighter and changing to Barium Yellow 503 at outer margin of petal.

*General color effect.*—Newly opened flower—Mimosa Yellow 602/1. Three days open—Barium Yellow 503/1.

*Behavior.*—Drop off cleanly.

*Flower longevity.*—On bush in garden 4 days in October; cut roses grown outdoors kept at living room temperatures 4 days in October.

*Reproductive organs*

Stamens: Many; arranged irregularly about pistils mixed with petaloids.
Filaments: Many; most with anthers; medium length. Color—Lemon Yellow 4.
Anthers: Open at various times; medium length. Color—yellow (general color effect). Occasionally an anther fused with a petaloid.
Pollen: Abundant; gold.
Pistils: Medium number.
Styles: Uneven; medium to long; medium size; bunched.
Stigma: Yellow.
Ovaries: Some protruding from receptacle.
Hips: None observed.

Sepals: Permanent; moderately long; straight spear shaped.

Seeds: None observed.

*Plant*

Foliage:

*Leaves.*—Compound of 3, but usually 5 leaflets; normal quantity; medium size; leathery.

*Leaflets.*—Shape—oval with apex acute; base obtuse; margin simply serrate. Color: mature—upper surface—Ivy Green 0001060/2; undersurface—Willow Green 000862/1; young—upper surface—Spinach Green 0960/2 overlaid with Oxblood Red 00823; undersurface—Fern Green 0862/2 overlaid with Oxblood Red 00823/3.

*Rachis (the supporting stem of the compound leaf).*—Medium size. Upper side—grooved hairy. Under side—sparsley prickly.

*Stipules.*—Moderately long; moderately narrow; with medium points; turning out at an angle of more than 45°.

*Disease.*—Resistance comparable to the average variety growing under the same cultural conditions.

Growth:

*Habit.*—Bushy, much branched.

*Growth.*—Vigorous.

*Canes.*—Medium.

*Main stems.*—Dull. Color—Parsley Green 00962/2. Prickles—several; color—brown (general color term). Hairs—none.

*Branches.*—Dull. Color—Parsley Green 00962/2. Prickles—several; color—reddish (general color term). Hairs—none.

*New shoots.*—Dull. Color—Fern Green 0862/1. Prickles—several; color—reddish base with greenish yellow tips (general color terms). Hairs—none.

I claim:

A new and distinct variety of floribunda rose plant substantially as herein shown and described, characterized by its good vigor and balanced habit, its good continuity of bloom, its flowers of extraordinarily large size during certain times of the year for a plant of the floribunda class, with a petal count of from 40 to 45, and the color of its blooms varying from Mimosa Yellow in newly opened blooms to Barium Yellow at maturity.

No references cited.

ABRAHAM G. STONE, *Primary Examiner.*